(12) United States Patent
Prasad et al.

(10) Patent No.: US 7,449,451 B2
(45) Date of Patent: *Nov. 11, 2008

(54) USE OF MULTIPLE ANTIOXIDANT MICRONUTRIENTS AS SYSTEMIC BIOLOGICAL RADIOPROTECTIVE AGENTS AGAINST POTENTIAL IONIZING RADIATION RISKS

(75) Inventors: Kedar N. Prasad, Denver, CO (US); Gerald M. Haase, Greenwood Village, CO (US); William C. Cole, Centennial, CO (US)

(73) Assignee: Premier Micronutrient Corporation, Nashville, TN (US)

( * ) Notice: Subject to any disclaimer, the term of this patent is extended or adjusted under 35 U.S.C. 154(b) by 144 days.

This patent is subject to a terminal disclaimer.

(21) Appl. No.: 10/229,274

(22) Filed: Aug. 28, 2002

(65) Prior Publication Data

US 2003/0064955 A1    Apr. 3, 2003

(51) Int. Cl.
*A61K 31/714* (2006.01)
*A61K 31/59* (2006.01)
*A61K 31/555* (2006.01)
*A61K 31/525* (2006.01)
*A61K 31/51* (2006.01)
*A61K 31/4184* (2006.01)
*A61K 31/015* (2006.01)

(52) U.S. Cl. .................. 514/52; 514/251; 514/184; 514/393; 514/350; 514/167; 514/474; 514/458; 514/440; 514/552; 514/276; 514/562; 514/494; 514/574; 514/763

(58) Field of Classification Search ............... 514/52, 514/167, 184, 251, 276, 350, 393, 440, 458, 514/474, 494, 552, 562, 574, 763, 188, 725
See application file for complete search history.

(56) References Cited

U.S. PATENT DOCUMENTS

| | | | |
|---|---|---|---|
| 2,939,821 A | 6/1960 | Freedman et al. | 514/52 |
| 3,446,899 A | 5/1969 | Magid et al. | 514/474 |
| 3,584,114 A | 6/1971 | Cavalli | 424/465 |
| 3,777,029 A | 12/1973 | Magid | 514/356 |
| 4,619,829 A | 10/1986 | Motschan | 424/602 |
| 4,740,373 A | 4/1988 | Kesselman et al. | 424/638 |
| 4,976,960 A | 12/1990 | Grossman et al. | 424/750 |
| 5,084,482 A | 1/1992 | Hirsch et al. | 514/562 |
| 5,223,285 A | 6/1993 | DeMichele et al. | 426/72 |
| 5,292,538 A * | 3/1994 | Paul et al. | 426/74 |
| 5,571,441 A | 11/1996 | Andon et al. | 252/1 |
| 5,626,883 A | 5/1997 | Paul | 424/605 |
| 5,629,023 A | 5/1997 | Bland | 424/655 |
| 5,788,971 A | 8/1998 | Togasaki | 424/729 |
| 5,922,346 A | 7/1999 | Hersh | 424/439 |
| 5,922,704 A | 7/1999 | Bland | 514/185 |
| 5,939,394 A | 8/1999 | Fleming et al. | 514/23 |
| 5,948,823 A | 9/1999 | Ben-Amotz | 514/763 |
| 5,976,568 A * | 11/1999 | Riley | 424/451 |
| 5,985,339 A | 11/1999 | Kamarei | 426/72 |
| 6,048,846 A | 4/2000 | Cochran | 514/168 |
| 6,066,327 A | 5/2000 | Gubernick | 424/401 |
| 6,068,848 A | 5/2000 | Gubernick | 424/401 |
| 6,080,788 A | 6/2000 | Sole et al. | 514/561 |
| 6,090,414 A * | 7/2000 | Passwater et al. | 424/702 |
| 6,117,872 A | 9/2000 | Maxwell et al. | 514/249 |
| 6,124,268 A | 9/2000 | Ghosad | 514/27 |
| 6,130,244 A | 10/2000 | DeMichele et al. | 514/474 |
| 6,162,468 A | 12/2000 | Stanley et al. | 424/600 |
| 6,194,452 B1 | 2/2001 | Murad | 514/474 |
| 6,245,360 B1 | 6/2001 | Markowitz | 424/641 |
| 6,254,898 B1 | 7/2001 | Bragaglia | 424/729 |
| 6,255,341 B1 | 7/2001 | DeMichele et al. | 514/474 |
| 6,258,384 B1 | 7/2001 | Stanley et al. | 424/600 |
| 6,291,533 B1 | 9/2001 | Fleischner | 514/682 |
| 6,326,034 B1 | 12/2001 | Mirsky et al. | 424/725 |
| 6,329,414 B1 | 12/2001 | Thomas et al. | 514/400 |
| 6,362,167 B1 | 3/2002 | Ghosal | 514/25 |
| 6,379,664 B1 | 4/2002 | Lou et al. | 424/94.5 |
| 6,426,076 B1 | 7/2002 | Pascoe | 424/400 |
| 6,426,362 B1 | 7/2002 | Miller et al. | 514/458 |
| 6,444,221 B1 | 9/2002 | Shaprio | 424/451 |
| 6,444,700 B1 | 9/2002 | DeMichele et al. | 514/474 |
| 6,451,341 B1 | 9/2002 | Slaga et al. | 424/468 |
| 6,573,299 B1 | 6/2003 | Petrus | 514/558 |
| 6,579,544 B1 | 6/2003 | Rosenberg et al. | 424/736 |
| 6,602,512 B1 | 8/2003 | Cavazza | 424/400 |
| 6,632,459 B2 | 10/2003 | Graus et al. | 424/728 |
| 6,660,293 B2 | 12/2003 | Giordano et al. | 424/439 |
| 6,753,325 B2 | 6/2004 | Rosenbloom | 514/167 |
| 6,770,663 B2 | 8/2004 | Wagle et al. | 514/365 |
| 6,797,729 B1 | 9/2004 | Byrne et al. | 514/562 |

(Continued)

OTHER PUBLICATIONS

"Anti-Irradiation Effect of Beta-Carotene and Vitamin E", Chen et al., Zhonghua Fangshe Yixue Yu Zazi, 1997, 17(2), 117-119, abstract.*

(Continued)

*Primary Examiner*—Brian-Yong S Kwon
(74) *Attorney, Agent, or Firm*—Dan M. DeLaRosa

(57) ABSTRACT

Disclosed herein is a method for protecting humans in need of such protection from physical damage caused by ionizing radiation comprising administering to said humans on a defined basis prior to and after exposure to such radiation a plurality of antioxidants at a dosage level directly proportional to the radiation level likely to be encountered.

7 Claims, No Drawings

U.S. PATENT DOCUMENTS

| | | | | |
|---|---|---|---|---|
| 6,805,880 | B1* | 10/2004 | Højgaard et al. | 424/468 |
| 6,814,983 | B2 | 11/2004 | Giordano et al. | 424/630 |
| 6,844,012 | B1 | 1/2005 | Forceville et al. | 424/702 |
| 6,849,613 | B2* | 2/2005 | Prasad et al. | 514/52 |
| 6,863,904 | B2 | 3/2005 | Giordano et al. | 424/638 |
| 2002/0146463 | A1 | 10/2002 | Clayton | 424/617 |
| 2002/0182196 | A1 | 12/2002 | McCleary | 424/94.1 |
| 2002/0182585 | A1 | 12/2002 | Kindness et al. | 435/4 |
| 2002/0193323 | A1 | 12/2002 | Yegorova | 514/33 |
| 2003/0055012 | A1 | 3/2003 | Carter | 514/42 |
| 2003/0103954 | A1 | 6/2003 | Rosenbloom | 424/94.1 |
| 2003/0104080 | A1 | 6/2003 | Singh | 424/729 |
| 2003/0105027 | A1 | 6/2003 | Rosenbloom | 514/18 |
| 2003/0108624 | A1 | 6/2003 | Kosbab | 424/729 |
| 2003/0119909 | A1 | 6/2003 | Stanislaus | 514/562 |
| 2003/0147981 | A1 | 8/2003 | Gillam | 424/770 |
| 2003/0161863 | A1 | 8/2003 | Ballevre et al. | 424/439 |
| 2003/0215430 | A1 | 11/2003 | Petrus | 424/94.1 |
| 2004/0043013 | A1 | 3/2004 | McCleary | 424/94.1 |
| 2004/0082536 | A1 | 4/2004 | Cooper et al. | 514/52 |
| 2004/0106674 | A1 | 6/2004 | Rich et al. | 514/458 |
| 2004/0109882 | A1 | 6/2004 | Schonrock | 424/401 |
| 2004/0223962 | A1 | 11/2004 | Riordan | 424/94.63 |
| 2005/0009779 | A1 | 1/2005 | Kiliaan et al. | 514/52 |

OTHER PUBLICATIONS

"Cysteine", University of Maryland Medical Center, 2002.*
"Multiple Myeloma", www.merck.com, 2003.*
"Baylor, St. Luke's study uses gene therapy as treatment for pancreatic cancer", www.bcm.edu, 2006.*
Cecil Textbook of Medicine, 20th Edition, vol. 1, 1997.*
Niki, E.; Mechanisms and dynamics of antioxidant action of ubiquinol. Mol Aspects Med. 18 Suppl:S63-70; 1997. (Abstract).
Jacob, S., Henriksen, L, et. al. (1995) Enhancement of glucose disposal in patients with type II diabetes by alpha-lipoic acid. Arzneim Forsch, 45: 872-874. (Abstract).
Suzuki YJ, Tsuchiya M, Packer L: Lipoate prevents glucose-induced protein modifications. Free Rad Res Commun 17:211-217, 1992. (Abstract).
Verlangieri, A. J., Bush, M. J.; Effects of d-alpha-tocopherol supplementation on experimentally induced primate atherosclerosis. J Am Coll Nutr. 11:131-138; 1992. (Abstract).
Hoogwerf, B. J., Young, J. B.; The Hope study. Ramipril lowered cardiovascular risk, but vitamin E did not. Cleve Clin J Med. 67:287-293; 2000. (Abstract).
Carter, C. A., Pogribny, M., Davidson, A., Jackson, C. D., McGarrity, L. J., Morris, S. M.; Effects of retionic acid on cell differentiation and recersion toward normal in human endometrial adenocarcinoma (RL95-2) cells. Anticancer Res. 16:17-24; 1996. (Abstract).
Salonen, J. T.; Clinical trials testing cardiovascular benefits of antioxidant supplementation. Free, Radic Res. 36:1299-1306; 2002. (Abstract).
International Council for Radiation Protection, ICRP publication 33, 1982.
*FDA Centers for Radiologic Health Handbook*: Selected Tissue Doses for Fluoroscopic and Cineangiographic Examination of the Coronary Arteries, 1995.
FDA and Mayo Clinic values of X-ray doses, www.mayohealth.org, Mayo Foundation for Medican Education and Research (2000).
Gopalakrishna, R., Gundimeda, U., Chen, Z. Vitamin E Succinate Inhibits Protein Kinase C: Correlation With Its Unique Inhibitory Effects On Cell Growth And Transformation. In: Prasad, K. N., Santamaria, L., Williams, R. M., eds. Nutrients In Cancer Prevention And Treatment. Totowa, New Jersey: Humana Press; 1995:21-37.
Frei, B., *Natural Antioxidants in Human Health and Disease*, Academic Press (1994).
Tasinato, A., Boscoboinik, D., Bartoli, G. M., Maroni, P., Azzi, A.; d-alpha-tocopherol inhibition of vascular smooth muscle cell proliferation occurs as physiological concentrations, correlates with protein kinase C inhibition, and is independent of its antioxidant properties. Proc Natl Acad Sci U S A. 92:12190-12194; 1995.
Radi, R., *Nitric oxide, oxidants, and protein tyrosine nitration*, The National Academy of Sciences of the USA (2004).
Tardif, J. C., Cote, G., Lesperance, J., Bourassa, M., Lambert, J., Doucet, S., Bilodeau, L., Nattel, S., de Guise, P.; Probucol and multivitamins in the prevention of restenosis after coronary angioplasty. Multivitamins and Probucol Study Group. N Engl J Med. 337:365-372; 1997.
Brown, B.G. et al., *Simvastatin and Niacin, Antioxidant Vitamins, or the Combination for the Prevention of Coronary Disease*, N Engl J Med 345:1583-1592; 2001.
Matthan, N.R. et al., Impact of Simvastatin, niacin, and/or antioxidants on cholesterol metabolism in CAD patients with low HDL, Journal of Lipid Research 44:800-806; 2003.
Gandhi VM, Wagh SS, Natraj CV, Menon KKG: Lipoic acid and diabetes II: mode of action of lipoic acid. J Biosci 9:117-127, 1985.
Earnest, C.P. et al., Complex Multivitamin Supplementation Improves Homocysteine and Resistance to LDL-C Oxidation, Journal of the American College of Nutrition 22:400-407; 2003.
Waters, D. D., Alderman, E. L., Hsia, J., Howard, B. V., Cobb, F. R., Rogers, W. J., Ouyang, P., Thompson, P., Tardif, J. C., Higginson, L., Bittner, V., Steffes, M., Gordon, D. J., Proschan, M., Younes, N., Verter, J. I.; Effects of hormone replacement therapy and antioxidant vitamin supplements on coronary atherosclerosis in postmenopausal women: a randomized controlled trial. Jama. 288:2432-2440; 2002.
Schnyder, G., Roffi, M., Flammer, Y., Pin, R., Hess, O. M.; Effect of homocysteine-lowering therapy with folic acid, vitamin B12, and vitamin B6 on clinical outcome after percutaneous coronary intervention: the Swiss Heart study: a randomized controlled trial. JAMA. 288:973-979; 2002.
Haugaard, N, Haugaard ES: Stimulation of glucose utilization by thioctic acid in rat diaphragm incubated in vitro. Biochem Biophys Acta, 222:583-586, 1970.
Singh HPP, Bowman RH: Effect of D, L-alpha lipoic acid on the citrate concentration and phosphofructokinase activity of perfused hearts from normal and diabetic rats. Biochem Biophys Res Commun 41:555-561, 1970.
Brenner DJ, Elliston CD, Hall EJ, Berdon WE: Estimated risks of radiation-induced fatal cancer from pediatric CT, Am J Roentgenol 176: 289-296, 2001.
Witztum, J. L.; The oxidation hypothesis of atherosclerosis. Lancet. 344:793-795; 1994.
Routine vitamin supplementation to prevent cancer and cardiovascular disease: recommendations and rationale. Ann Intern Med. 139:51-55; 2003.
Prasad KN, Cole WC, and Haase GM: Health risk of low dose ionizing radiation in humans: A review. Exp. Biol Med 229:378-382, 2004.
Riley, S. J., Stouffer, G. A.; Cardiology Grand Rounds from the University of North Carolina at Chapel Hill. The antioxidant vitamins and coronary heart disease: Part 1. Basic science background and clinical observational studies. Am J Med Sci. 324:314-320; 2002.
Riley, S. J., Stouffer, G. A.; Cardiology Grand Rounds from the University of North Carolina at Chapel Hill. The antioxidant vitamins and coronary heart disease: Part II. Randomized clinical trials. Am J Med Sci. 325:15-19; 2003.
Morris, C. D., Carson, S.; Routine vitamin supplementation to prevent cardiovascular disease: a summary of the evidence for the U.S. Preventive Services Task Force. Ann Intern Med. 139:56-70; 2003.
Reaven, P. D., Khouw, A., Beltz, W. F., Parthasarathy, S., Witztum, J. L.; Effect of dietary antioxidant combinations in humans. Protection of LDL by vitamin E but not by beta-carotene. Arterioscler Thromb. 13:590-600; 1993.
de Nigris, F., Youssef, T., Ciafre, S., Franconi, F., Anania, V., Condorelli, G., Palinski, W., Napoli, C.; Evidence for oxidative activation of c-Myc-dependent nuclear signaling in human coronary smooth muscle cells and in early lesions of Watanabe heritable hyperlipidemic rabbits: protective effects of vitamin E. Circualtion. 102:2111-2117; 2000.
Mann, M. J., Whittemore, A. D., Donaldson, M. C., Belkin, M., Conte M. S., Polak, J. F., Orav, E. J., Ehsan, A., Dell'Acqua, G., Dzau, V. J.;

Ex-vivo gene therapy of human vascular bypass grafts with E2F decoy: the Prevent single-centre, randomised, controlled trial. Lancet. 354:1493-1498; 1999.

Becker, A.E., de Boer, O.J., van Der Wal, A. C.; The role of inflammation and infection in coronary artery disease. Annu Rev Med. 52:289-297; 2001.

Napoli, C., Ignarro, L. J.; Nitric oxide and atherosclerosis. Nitric Oxide. 5:88-97; 2001.

Ignarro, L. J., Cirino, G., Casini, A., Napoli, C.; Nitric oxide as a signaling molecule in the vascular system: an overview. J Cardiovasc Pharmacol. 34:879-886; 1999.

Anderson, T. J., Gerhard, M. D., Meredith, I. T., Charbonneau, F., Delagrange, D., Creager, M. A., Selwyn, A. P., Ganz, P.; Systemic nature of endothelial dysfunction in atherosclerosis. Am J Cardiol. 75:71B-74B; 1995.

Drexler, H.; Nitric oxide and coronary endothelial dysfunction in humans. Cardiovasc Res. 43:572-579; 1999.

Luoma, J. S., Yla-Herttuala, S.; Expression of inducible nitric oxide synthase in macrophages and smooth muscle cells in various types of human atherosclerotic lesions. Virchows Arch. 434:561-568; 1999.

Gum, P. A., Kottke-Marchant, K., Welsh, P. A., White, J., Topol, E. J.; A prospective, blinded determination of the natural history of aspirin resistance among stable patients with cardiovascular disease. J Am Coll Cardiol. 41:961-965; 2003.

Cotter, G., Shemesh, E., Zehavi, M., Dinur, I., Rudnick, A., Milo, O., Vered, Z., Krakover, R., Kaluski, E., Kornberg, A.; Lack of aspirin effect: apsirin resistance or resistance to taking aspirin? Am Heart J. 147:293-300; 2004.

Gum, P. A., Kottke-Merchant, K., Poggio, E. D., Gurm, H., Welsh, P. A., Brooks, L., Sapp, S. K., Topol, E. J.; Profile and prevalence of aspirin resistance in patients with cardiovascular disease. Am J Cardiol. 88:230-235; 2001.

Lynch, S., Frei, B. Antioxidants as Antiatherogens: Animal Studies. In: Frei, B., ed. Natural Antioxidants in Human Health and Disease. New York: Academic Press; 1994:353-385.

Smith, T. L., Kummerow, F. A.; Effect of dietary vitamin E on plasma lipids and atherogenesis in restricted ovulator chickens. Atherosclerosis. 75:705-709; 1989.

Wojcicki, J., Rozewicka, L., Barcew-Wiszniewska, B., Samochowiec, L., Juzwiak, S., Kadlubowska, D., Tustanowski, S., Juzyszyn, Z.; Effect of selenium and vitamin E on the development of experimental atherosclerosis in rabbits. Atherosclerosis. 87:9-16; 1991.

Calzada, C., Bruckdorfer, K. R., Rice-Evans, C. A.; The Influence of antioxidant nutrients on platelet function in healthy volunteers. Atherosclerosis. 128:97-105; 1997.

Colette, C., Pares-Herbute, N., Monnier, L. H., Cartry, E.; Platelet function in type I disbetes: effects of supplementation with large doses of vitamin E. Am J Clin Nutr. 47:256-261; 1988.

de Lorgeril, M., Boissonnat, P., Salen, P., Monjaud, I., Monnez, C., Guidollet, J., Ferrera, R., Dureau, G., Ninet, J., Renaud, S.; The beneficial effect of dietary antioxidant supplementation on platelet aggregation and cyclosporine treatment in heart transplant recipients. Transplantation. 58:193-195; 1994.

Adams, M. R., Kinlay, S., Blake, G. J., Orford, J. L., Ganz, P., Selwyn, A. P.; Atherogenic lipids and endothelial dysfunction: mechanisms in the genesis of ischemic syndromes. Annu Rev Med. 51:149-167; 2000.

Cohrs, R. J., Torelli, S., Prasad, K. N., Edwards-Prasad, J., Sharma, O. K.; Effect of vitamin E succinate and a cAMP-stimulating agent on the expression of c-myc and N-myc and H-ras in murine neuroblastoma cells. Int J Dev Neurosci. 9:187-194; 1991.

Gey, K. F., Puska, P.; Plasma vitamins E and A inversely correlated to mortality from ischemic heart disease in cross-cultural epidemiology. Ann N Y Acad Sci. 570:268-282; 1989.

Riemersma, R. A., Wood, D. A., Macintyre, C. C., Elton, R. A., Gey, K. F., Oliver, M. F.; Risk of angina pectoris and plasma concentrations of vitamins A, C, and E and carotene. Lancet. 337:1-5; 1991.

Rimm, E. B., Stampfer, M. J., Ascherio, A., Giovannucci, E., Colditz, G. A., Willett, W. C.; Vitamin E consumption and the risk of coronary heart disease in men. N Engl J Med. 328:1450-1456; 1993. (Abstract).

Stampfer, M. J., Hennekens, C. H., Manson, J. E., Colditz, G. A., Rosner, B., Willett, W. C.; Vitamin E consumption and the risk of coronary disease in women. N Engl J Med. 328:1444-1449; 1993. (Abstract).

Losonczy, K. G., Harris, T. B., Havlik, R. J.; Vitamin E and vitamin C supplement use and risk of all-cause and coronary heart disease mortality in older persons: the Established Populations for Epidemiologic Studies of the Elderly. Am J Clin Nutr. 64:190-196; 1996.

Salonen, J. T., Salonen, R., Penttila, I., Herranen, J., Jauhiainen, M., Kantola, M., Lappetelainen, R., Maenpaa, P. H., Alfthan, G., Puska, P.; Serum fatty acids, apolipoproteins selenium and vitamin antioxidants and the risk of death from coronary artery disease. Am J Cardiol. 56:226-231; 1985.

Kok, F. J., de Bruijn, A. M., Vermeeren, R., Hofman, A., van Laar, A., de Bruin, M., Hermus, R. J., Valkenburg, H. A.; Seru, selenium, vitamin antioxidants, and cardiovascular mortality; a 9-year follow-up study in the Netherlands. Am J Clin Nutr. 45:462-468; 1987.

Heitzer, T., Yla Herttuala, S., Wild, E., Luoma, J., Drexler, H.; Effect of vitamin E on endothelial vasodilator function in patients with hypercholesterolemia, chronic smoking or both. J Am Coll Cardiol. 33:499-505; 1999.

Wilkinson, I. B., Megson, I. L., MacCallum, T., Rooijmans, D. F., Johnson, S. M. Boyd, J. L., Cockcroft, J. R., Webb, D. J.; Acute methionine loading does not alter arterial stiffness in humans. J Cardiovasc Pharmacol. 37:1-5; 2001.

Stephens, N. G., Parsons, A., Schofield, P. M., Kelly, F., Cheeseman, K., Mitchinson, M. J.; Randomised controlled trial of vitamin E in patients with coronary disease: Cambridge Heart Antioxidant Study (CHAOS). Lancet. 347:781-786; 1996.

Jialal, I., Devaraj, S.; Vitamin E supplementation and cardiovascular events in high-risk patients. N Engl J Med. 342:1917-1918; 2000.

Weinberg, R. B., VanderWerken, B. S., Anderson, R. A., Stegner, J. E., Thomas, M. J.; Pro-oxidant effect of vitamin E in cigarette smokers consuming a high polyunsaturated fat diet. Arterioscler Thromb Vasc Biol. 21:1029-1033; 2001.

DeMaio, S. J., King, S. B., 3rd Lembo, N. J., Roubin, G. S., Hearn, J. A., Bhagavan, H. N., Sgoutas, D. S.; Vitamin E supplementation, plasma lipids and incidence of restenosis after percutaneous transluminal coronary angioplasty (PTCA). J Am Coll Nutr. 11:68-73; 1992.

Devaraj, S., Jialal, I.; Alpha tocopherol supplementation decreases serum C-reactive protein and monocyte interleukin-6 levels in normal volunteers and type 2 diabetic patients. Free Radic Biol Med. 29:790-792; 2000.

Islam, K. N., O'Byrne, D., Devaraj, S., Palmer, B., Grundy, S. M., Jialal, I.; Alpha-tocopherol supplementation decreases the oxidative susceptibility of LDL in renal failure patients on dialysis therapy. Atherosclerosis. 150:217-224; 2000.

Rapola, J. M., Virtamo, J., Ripatti, S., Huttunen, J. K., Albanes, D., Taylor, P. R., Heinonen, O. P.; Randomised trial of alpha-tocopherol and beta-carotene supplements on incidence of major coronary events in men with previous myocardial infarction. Lancet. 349:1715-1720; 1997.

Frang, J. C., Kinlay, S., Beltrame, J., Hikiti, H., Wainstein, M., Behrendt, D., Suh, J., Frei, B., Mudge, G. H., Selwyn, A. P. Ganz, P.; Effect of vitamins C and E on progression of transplant-associated arteriosclerosis: a randomised trial. Lancet. 359:1108-1113; 2002.

Upritchard, J. E., Sutherland, W. H., Mann, J. I.; Effect of supplementation with tomato juice, vitamin E, and vitamin C on LDL oxidation and products of inflammatory activity in type 2 diabetes. Diabetes Care. 23:733-738; 2000.

Beckman, J. A., Goldfine, A. B., Gordon, M. B., Creager, M. A.; Ascorbate restores endothelium-dependent vasodilation impaired by acute hyperglycemia in humans. Circulation. 103:1618-1623; 2001.

Plotnick, G. D., Corretti, M. C., Vogel, R. A.; Effect of antioxidant vitamins on the transient impairment of endothelium-dependent brachial artery vasoactivity following a single high-fat meal. Jama. 278:1682-1686; 1997.

Redlich, C. A., Chung, J. S., Cullen, M. R., Blaner, W. S., Van Bennekum, A. M., Berglund, L.; Effect of long-term beta-carotene and vitamin A on serum cholesterol and triglyceride levels among participants in the Carotene and Retinol Efficacy Trial (CARET). Atherosclerosis. 143:427-434; 1999.

Neunteufl, T., Kostner, K., Katzenschlager, R., Zehetgruber, M., Maurer, G., Weidinger, F.; Additional benefit of vitamin E supplementation to simvastatin therapy on vasoreactivity of the brachial artery of hypercholesterolemic men. J Am Coll Cardiol. 32:711-716; 1998.

Langsjoen, P. H., Folkers, K.; Long-term efficacy and safety of coenzyme Q10 therapy for idiopathic dilated cardiomyopathy. Am J Cardiol. 65:521-523; 1990.

Hodis, H. N., Mack, W. J., LaBree, L., Cashin-Hemphill, L., Sevanian, A., Johnson, R., Azen, S.P.; Serial coronary angiographic evidence that antioxidant vitamin intake reduces progression of coronary artery atherosclerosis. Jama. 273:1849-1854; 1995.

Collins, R., Peto, R., Armitage, J.; The MRC/BHF Heart Protection Study: preliminary results. Int J Clin Pract. 56:53-56; 2002.

Cheung, M. C., Zhao, X. Q., Chair, A., Albers, J. J., Brown, B. G.; Antioxidant supplements block the response of HDL to simvastatin-niacin therapy in patients with coronary artery disease and low HDL. Arterioscler Thromb Vasc Biol. 21:1320-1326; 2001.

Zhang, L. X., Cooney, R. V., Bertram, J. S.; Carotenoids up-regulate connexin43 gene expression independent of their provitamin A or antioxidant properties. Cancer Res. 52:5707-5712; 1992.

Hazuka, M. B., Edwards-Prasad, J., Newman, F., Kinzie, J. J., Prasad, K. N.; Beta-carotene induces morphological differentiation and decreases adenylate cyclase activity in melanoma cells in culture. J Am Coll Nutr. 9:143-149; 1990.

Jessup, W.; Oxidized lipoproteins and nitric oxide. Curr Opin Lipidol. 7:274-280; 1996. (Abstract).

Vile, G. F., Winterbourn, C. C.; Inhibition of adriamycin-promoted microsomal lipid peroxidation by beta-carotene, alpha-tocopherol and retinol at high and low oxygen partial pressures. FEBS Lett. 238:353-356; 1988.

Niki, E.; Interaction of ascorbate and alpha-tocopherol. Ann N Y Acad Sci. 498:186-199; 1987.

Prasad, K. N., Kumar, B., Yan, X. D., Hanson, A. J., Cole, W. C.; Alpha-tocopheryl succinate, the most effective form of vitamin E for adjuvant cancer treatment: a review. J Am Coll Nutr. 22:108-117; 2003.

Ingold, K. U., Burton, G. W., Foster, D. O., Hughes, L., Lindsay, D. A., Webb, A.; Biokinetics of and discrimination between dietary RRR- and SRR-alpha-tocopherols in the male rat. Lipids. 22:163-172; 1987.

Witschi, A., Reddy, S., Stofer, B., Lauterburg, B. H.; The systemic availability of oral glutathione. Eur J Clin Pharmacol. 43:667-669; 1992.

Stoyanovsky, D. A., Osipov, A. N., Quinn, P. J., Kagan, V. E.; Ubiquinone-dependent recycling of vitamin E radicals by superoxide. Arch Biochem Biophys. 323:343-351; 1995.

Abate, A., Yang, G., Dennery, P. A., Oberle, S., Schroder, H.; Synergistic inhibition of cyclooxygenase-2 expression by vitamin E and aspirin. Free Radic Biol Med. 29:1135-1142; 2000.

Alessio H. (1993). Exercise-induced oxidative stress. Medicine & Science in Sports & Exercise, 25:218-22.

Clarkson PM, Nosaka K & Braun B. (1992). Muscle function after exercise-induced muscle damage and rapid adaptation. Medicine & Science in Sports & Exercise, 24:512-520.

Halliwell B, Gutteridge JM & Cross CE. (1992). Free radicals, antioxidants and human disease: where are we now? Journal Laboratory Clinical Medicine, 119:598-620.

Jenkins PR & Goldfarb A (1993). Introduction: oxidant stress, aging, and exercise. Medicine & Science in Sports & Exercise, 25:210-212.

Meydani M, Evans WJ, Handelman G, biddle L, Fielding RA, Meydani SN, Burrill J, Fiatarone MA, Blumberg IB, & Cannonn JG (1994). Protective effect of vitamin E on exercise-induced oxidative damage in young and old adults. American Journal of Physiology, 264:R992.

Nagamatsu, M., Nickander, K.K., Schmelzer, J.D. et al. (1995). Lipoic acid improves nerve blood flow, reduces oxidative stress and improves distal nerve conduction in experimental diabetic neuropathy. Diabetes Care, 18: 1160-1167.

Pfeiffer JM, Askew EW, Roberts DE, Wood Sm, Benson JE, Johnson SC & Freedman MS (1999). Effect of antioxidant supplementation on urine and blood markers of oxidative stress during extended moderate-altitude training. Wilderness and Environmental Medicine, 10:66-7 Physician Desk Ref.

Prasad, K.N., Cole W. and Hovland P. (1998) Cancer prevention studies: past, present and future direactions. Nutrition ,14: 197-210.

Natraj CV, Gandhi, VM, Menon KKG: Lipoic acid and Diabetes I: effect of dihydrolipoic acid administration in diabetic rats and rabbits. J. Biosci 6:37-46, 1984.

Wagh SS, Gandi VM, Natraj CV, Menon KKG: Lipoic acid and diabetes-III: metabolic role of acetyl dihydrolipoic acid. J Biosci 10:171-179, 1986.

Faust A, Burkart V, Ulrich H, Weischer CH, Kolb H: Effect of lipoic acid on cyclophosphamide-induced diabetes and insulinitis in non-obese diabetic mice. Int. J. Immunopharmacol 16:61-66, 1994.

Barish, R.J., "In-Flight Radiation: Counseling Patients About Risk", *The Journal of the American Board of Family Practice*, 12(3):195-199 (1999).

Barish, R.J., "Health Physics Concerns In Commercial Aviation", *Health Physics (The Radiation Protection Journal)*, 59(2):199-204 (1990).

Narra, V.R., et al., "Vitamins as Radioprotectors In Vivo, I. Protection by Vitamin C against Internal Radionuclides in Mouse Testes: Implications to the Mechanism of Damage Caused by the Auger Effect", *Radiation Research, An International Journal*, 137(3):394-399 (1994).

Gaziev, A.I., et al., "Effect of vitamin-antioxidant micronutrients on the frequency of spontaneous and in-vitro γ-ray-induced micronuclei in lymphocytes of donors: the age factor", *Carcinogenesis*, 17(3):493-499 (1996).

Kumar, K.S., et al., "Nutritional Approaches to Radioprotection: Vitamin E", *Military Medicine*, 167(2):57-59 (2002).

Institute of Medicine Report: "Potential Radiation Exposure in Military Operations, Protecting the Soldier Before, During and After", http://www.nap.edu/openbook/0309064392/mtml/55.html, National Academy Press (2000).

DiPaolo, J.A., et al., "In vitro morphologic transformation of Syrian hamster cells by U.V.-irradiation is enhanced by X-irradiation and unaffected by chemical carcinogens", *International Journal Radiat. Biol.*, 30(1):41-53 (1976).

Allard, D.J., CRCPD Liaison to NCRP, (G50) Report on the 2004 Annual Meeting of the NCRP, http://www.crcpd.org/Reports_on__ Mtgs/NCRP_Apr04.htm.

"Long term consequences of terrorism involving radiation exposure and the release of radioactive materials" 2004.

Liptak, G.S., "The Child Who Has Severe Neurologic Impairment", *Physical Assessment*, 45(1):123-144 (1998).

Paterson A., et al., "Helical CT of the Body: Are Settings Adjusted for Pediatric Patients?", *Am. J. Roentgenol*, 176:297-301 (2001).

Patel B., et al., "Compatibility of calcipotriene with other topical medications", *Journal of the American Academy of Dermatology*, 38:1010-1011 (1998).

Revell, G.M., et al., "Understanding the Child With Special Health Care Needs: A Developmental Perspective", *Journal of Pediatric Nursing*, 6(4):258-268 (1991).

Borek, C., et al., "Selenium and vitamin E inhibit radiogenic and chemically induced transformation in vitro via different mechanisms", *Proc. Natl. Acad. Sci. USA*, 83:1490-1494 (1986).

Stanford W., et al., "Coronary Artery Calcification: Clinical Significance and Current Methods of Detection", *Am. J. Roentgenol*, 161:1139-1146 (1993).

Cascade P.N., et al., "Radiation Exposure to Patients Undergoing Percutaneous Transluminal Cooronary Angioplasty", *Am. J. Cardiol.*, 59:996-997 (1987).

Weiss, J.F., et al., "Radioprotection by Antioxidants", *Annals New York Academy of Sciences*, 899:44-60 (2000).

Sminia P, et al., "Hyperthermia, radiation carcinogenesis and the protective potential of vitamin A and N-acetylcysteine", *J. Cancer Res. Clin. Oncol.*, 122:343-350 (1996).

Ushakova, T., et al., "Modification of Gene Expression By Dietary Antioxidants in Radiation-Induced Apoptosis of Mice Splenocytes", *Free Radical Biology & Medicine*, 26(7-8):887-891 (1999).

Rumberger, J.A., et al., "Coronary Heart Disease/Platelet Activation/ Myocardial Infarction: Coronary Calcium, as Determinted by Electron Beam Computed Tomography, and Coronary Disease on Arteriogram: Effect of Patient's Sex on Diagnosis" *American Heart Association*, 91(5):1363-1367 (1995).

Ben-Amotz, A., et al., "Effect of natural β-carotene supplementation in children exposed to radiation from the Chernobyl accident", *Radiat. Environ. Biophys.*, 37:187-193 (1998).

Gaziev, A.I., et al., "Dietary supplements of antioxidants reduce hprt mutant frequency in splenocytes of aging mice", *Mutation Research*, 338:77-86 (1995).

Mutlu-Türkogly, Ü., et al., "The Effect of Selenium and/or Vitamin E Treatments On Radiation—Induced Intestinal Injury in Rats", *Life Sciences*, 66(20):1905-1913 (2000).

Dion, P.W., et al., "The effect of dietary ascorbic acid and α-tocopherol on fecal mutagenicity", *Mutation Research*, 102:27-37 (1982).

El-Habit, O.H.M., et al., "The modifying effect of β-carotene on gamma radiation-induced elevation of oxidative reactions and genotoxicity in male rats", *Mutation Research*, 466-179-186 (2000).

Krinsky, N.I., "Antioxidant Functions of Carotenoids", *Free Radical Biology & Medicine*, 7:617-635 (1989).

Ryabchenko, N.I., et al., "Molecular, Cellular and System. Mechanisms of Radioprotective Action of Polyvitamine Antioxidant Composites" *Radiatsionnaia Biologiia*, 36:895-899 (1996) (In Russian).

Umegaki, K., et al., "Feeding mice palm carotene prevents DNA damage in bone marrow and reduction of peripheral leukocyte counts, and enhances survival following X-ray irradiation", *Carcinogenesis*, 18(10)1943-1947 (1997).

Radner, B.S., et al., "Suppression of X-Ray Induced Transformation By Vitamin E In Mouse C3H/10T ½ Cells", *Cancer Letters*, 32-35-32 (1986).

Carini, R., et al., "Comparative Evaluation of the Antioxidant Activity of α-Tocopherol, α-Tocopherol Polyethylene Glycol 1000 Succinate and α-Tocopherol Succinate in Isolated Hepatocytes And Liver Microsomal Suspensions", *Biochemical Pharmacology*, 39(10) 1597-1601 (1990).

O'Connor, M.K., et al., "A radioprotectice effect of vitamin C observed in Chinese hamster ovary cells", *British Journal of radiology*, 50:587-591 (1977).

Presad, K.N., et al., "Effects of Tocopherol (Vitamin E) Acid Succinate on Morphological Alteractions and Growth Inhibition in Melanoma Cells in Culture", *Cancer Research*, 42:550-555 (1992).

Borek, C., et al., "Ozone acts alone and synergistically with ionizing to induce in vitro neoplastic transformation", *Carcinogenesis*, 7(9):1611-1613 (1986).

Knekt, P., et al., "Body Iron Stores and Risk of Cancer", *Int. J. Cancer*, 56:379-382 (1994).

Holtzman, S., et al., "Synergism of Estrogens and X-Rays in Mammary Carcinogenesis in Female ACI Rats", *J. Natl. Cancer Inst.*, 67(2):455-459 (1981).

Angioplasty and Cardiac Revascularization Treatment and Statistics, American Heart Associate, Heart and Stroke Statistical Update, (2001).

Paranich, A.V., et al., "The role of fat soluble vitamin A and vitamin E in preventing the biological effects of ionizing radiation in rat tissue" *Radiobiologia*, 32:743 (1992).

Prasad, K.N., *Human Radiation Biology*, Harper and Row, New York (1974).

Prasad, K.N., *Handbook of Radiobiology, Second Edition*, CRC Press, Florida (1994).

Radiation Dose Estimates for Radiopharmaceuticals, Radiation Internal Dose Information Center, Oak Ridge Institute for Science and Education (1996).

Og, Ni, et al., "Effect of beta-carotene on 60Co-gamma induced mutation at T-lymphocyte hypoxanthine-guanine phosphoribosyl transferace locus in rats", *Pharmacologic Sinica*, 18:535 (1997).

Stoker, M., "Effect of X-Irradiation on Susceptibility of Cells to Transformation by Polyoma Virus", *Nature*, 200:756-758 (1963).

Ramakrishnan, N., et al., "Radioprotection of Hematopoietic Tissues in Mice by Lipoic Acid", *Radiation ResearchI*, 130:360-365 (1992).

Killoran, P.L., et al., "Inhibition of Store-Operated Calcium Entry in Human Lymphocytes by Radiation: Protection by Glutathione", *Radiation Research*, 152:611-621 (1999).

Prasad, K.N., et al., "Protective effect of β-mercaptoethylamine and mesenteric vessel clamping on intestine-irradiated rats", *Int. J. Rad. Biol.*, 6(3):257-269 (1962).

Kennedy A.R., et al., "Effects of Retinoids, β-Carotene, and Canthaxanthin on UV- and X-Ray-Induced Transformation of C3H10T1/2 Cells in Vitro", *Nutr. Cancer*, 22:219-232 (1994).

Prasad, K.N., "Modification of the Effect of Tamoxifen cis-Platin DTIC, and Interferon-α2β on Human Melanoma Cells in Culture by a Micture of Vitamins", *Nutr. Cancer*, 22:233-245 (1994).

Puck, T.T., et al., "Caffeine Enhanced Measurements of Mutagenesis by Low Levels of γ-Irradiation in Human Lymphocytes", *Somatic Cell and Molecular Genetics*, 19(5):423-429 (1993).

Little, J.B., et al., "Influence of Noncarcinogenic Secondary Factors on Radiation Carcinogenesis", *Radiation Research*, 87:240-250 (1981).

Harapanhalli, R.S., et al., "Antioxidant Effects of Vitamin C in Mice Following X-Irradiation", *Research Communications in Molecular Pathology and Pharmacology*, 94(3):271-287 (1996).

Konopacka, M., et al., "Modifying effect of vitamins C, E and beta-carotene against gamma-ray induced DNA damage in mouse cells", *Mutation ResearchI*, 417:85-94 (1998).

Pollack, E.J., etl a., "Radiation Enhancement of SV40 Transformation in 3T3 and Human Cells", *Nature*, 219:520521 (1968).

Sinclair W.K., "Cysteamine: Differential X-ray Protective Effect on Chinese Hamster Cells During the Cell Cycle", *Science*, 159:442-444 (1968).

*Drug Information for the Healthcare Professional*, Rockville, MD: United States Pharmacopeial Convention, Inc., 2457 (1991).

Hall, E.J., *Radiobiology for the Radiologist*, J.B. Lippincott Co., Philadelphia, PA, (1994).

Wolf, S., "Ch. 6 Radiation Genetics", *Mechanisms in Radiobiology*, Errera M. and Forsberg A., Eds. Academic Press, New York, 441 (1961).

Thomson, J.F., *Radiation Protection In Mammals*, Reinhold, New York, NY (1962).

DiPaolo, J.A., et al., "Kinetics of Syrian Hamster Cells during X-Irradiation Enhancement of Transformation in Vitro by Chemical Carcinogen", *Radiation Research*, 66:310-325 (1976).

*Sources and Effects of Ionizing Radiation*, United States Scientific Committee on the Effects of Atomic Radiation UNSCEAR 2000 Report to the General Assembly, with Scientific Annexes, vols. 1 and 2.

Wagh, S.S, et al., "Mode of action of lipopic acid in diabetes", *J. Biosci.*, 11(1-4):59-74 (1987).

Niki, E., "Mechanisms and Dynamics of Antioxidant Action of Ubiquinol", *Molec. Aspects Med.*, 18:s63-s70 (1997).

Frei, B., "On the Role of Vitamin C and Other Antioxidants in Atherogenesis and Vascular Dysfunction", *Vascular Effects of Antioxidants*, 222(3):196-204 (1999).

Ji, Li Li, "Antioxidants and Oxidative Stress in Exercise", *Antioxidants and Oxidative Stress in Exercise*, 283-292 (1999).

Leeuwenburgh, C., et al., "Oxidative Stress and Antioxidants in Exercise", *Current Medicinal Chemistry*, 8:829-838 (2001).

Holvoet, P., et al., "Oxidized lipoproteins in atherosclerosis and thrombosis", *The FASEB journal*, 8(15):1279-1284 (1994).

Simon-Schnass I (1994). Risk of oxidative stress during exercise at high altitude. In: Sen CK, Packer L, Hanninen O, eds. Exercise and oxygen toxicity. New York, NY: Elsevier Science B.V., 191-210.

Renold AE, Mintz DH, Muller WA, Cahill, Jr GF: Diabetes mellitus: In: Stanbury JB, Wyngaarden JB, and Frederickson DS, eds. The metabolis basis of inherited diseases. New York: McGraw-Hill, 80-109, 1978.

Suzuki YJ, Tsuchiya M, Packer L: Lipoate prevents glucose-induced protein modifications. Free Rad Res Commun 17:211-217, 1992.

Salonen, J. T.; Clinical trials testing cardiovascular benefits of antioxidant supplementation. Free Radic Res. 36:1299-1306; 2002.

Carter, C. A., Pogribny, M., Davidson, A., Jackson, C. D., McGarrity, L. J., Morris, S. M.; Effects of retionic acid on cell differentiation and reversion toward normal in human endometrial adenocarcinoma (RL95-2) cells. Anticancer Res. 16:17-24; 1996.

Burkart V, Kioke T, Brenner HH, Imai Y, Kolb H: Dihydrolipoic acid protects pancreatic islet cells from inflammatory attack. Agents Actions 38:60-65, 1993.

* cited by examiner

USE OF MULTIPLE ANTIOXIDANT MICRONUTRIENTS AS SYSTEMIC BIOLOGICAL RADIOPROTECTIVE AGENTS AGAINST POTENTIAL IONIZING RADIATION RISKS

BACKGROUND OF THE INVENTION

1. Field of the Invention

The present invention relates to the use of antioxidants to reduce the effects of radiation on humans.

2. Description of Related Art

Ionizing radiation (X-rays and gamma rays) has proven to be a double-edged sword in clinical medicine since its discovery by Dr. Wilhelm Roentgen in 1895 (1, 2). Energy wavelength progresses along the electromagnetic continuum from longer ranges (radiowaves, microwaves, infrared, heat waves) to medium wavelengths (visible light, ultraviolet light) to shorter wavelengths (ionizing radiation, e.g., x-rays and gamma rays). It is these x-rays and gamma rays that are able to drive electrons out of their normal atomic orbits with enough kinetic energy to generate charged molecules (including free radicals) that damage cells. In addition to the initial realization by the medical community that ionizing radiation could detect as well as treat human diseases, came the unfortunate demonstration that it could also induce serious illness.

In fact, most of the ionizing radiation to which the human population is exposed, other than that received from environmental sources, is from the diagnostic and screening imaging machines employed by today's clinical healthcare professionals. For example, in the past, x-ray-induced skin cancers were noted with higher frequency in radiologists. Obviously, whenever x-rays are employed, it is done with caution so that patients and healthcare providers are exposed to as low a dose as possible. Physicists and nuclear engineers have devised improved equipment and radiation beam delivery systems to reduce the level of diagnostic radiation dose without compromising the quality of images. However, radiation biologists agree that there is no threshold dose below which there is no risk of cellular damage. In fact, even a single radiation track that crosses a cellular nucleus has a very low, but finite, probability of generating damage that may result in cellular dysfunction, structural mutations, and subsequent genetic implications.

While most clinical radiologists believe the risks of x-ray exposure are very small, residual biologic effects from alteration in structure are dependent on whether the cell repairs its injured components. Although the vast majority of damage is repaired, some may be unrepaired or misrepaired and therein lies the problem. In adults, most radiation researchers consider cancer induction to be the most important somatic effect of low dose ionizing radiation and this outcome may occur in nearly all the tissues of the human body. Academic radiologists are also raising future disease concerns regarding pediatric age groups because of the increased numbers of imaging studies now being performed in younger populations (3). In light of these concepts, the healthcare profession states that ionizing radiation exposure should only occur when there is a defined healthcare benefit, or indicated when the risk-benefit ratio is favorable to the patient. The critical concept has been always to protect humans by physical local factors, such as shielding and decreasing doses and x-ray times. However, no one has previously considered the additional aspects related to a strategy of systemic biological protection.

Recent advances in imaging technology have made possible the detection of many illnesses such as heart disease, cancer, neurologic diseases, arthritis and other acute or chronic conditions. It is also a significant development that this technology may detect the problem at an early stage when treatment interventions allow for less invasive therapeutic procedures and/or surgical operations and yet achieve improved health outcomes. In this environment, the number of diagnostic x-rays performed is truly enormous. It was estimated in the United States for the period 1985 to 1990 at least 800 diagnostic studies per 1,000 population were performed and this excluded dental x-rays and nuclear medicine (4). The importance of these findings can be appreciated since it is probable that frequent low dose radiation exposures may be more damaging than a single higher dose exposure on the criteria of gene mutations and cancer promotion.

The current era has seen an explosion of diagnostic imaging equipment including the introduction of computed tomography, digital radiography, expanded nuclear medicine applications, interventional radiology, and lengthening fluoroscopic procedures. In concert with these technical innovations, the concept of early disease detection and screening large populations to employ illness prevention strategies will generate further rapid expansion of members of imaging studies with increased ionizing radiation exposure to the public. As a direct consequence of this new proactive healthcare approach, imaging will be performed in many more, otherwise healthy, people and asymptomatic "at risk" populations. In addition, initial exposures will occur at an earlier age and the mandate of serial follow-up imaging will result in an overall greater frequency of x-ray studies.

The doses of ionizing radiation exposure in imaging studies vary dramatically from less than 0.1 rem (1 millisievert, mSv, for x-rays and gamma rays, 1 rem=1 rad) per test for some procedures to others that involve levels in some organs in excess of 25 rem per test. Table 1 lists a sampling of common studies (5-8). Note that while the red marrow dose is usually the reported "standard," the actual target organ dose is actually often significantly higher. For example, mammography exposes the actual breast tissue to approximately 700 mrem, virtually equal to the total skin entrance dose. Likewise, thallium scanning exposes the thorax to approximately 1000 mrem, about 20 times the red marrow dose.

TABLE 1

| Procedure | Effective Dose Equivalent (HE) | | Skin Entrance Dose |
|---|---|---|---|
| Diagnostic X-ray | mSv* | mrem | mrem |
| Chest AP, 100 kVp | 0.015 | 1.5 | 10 |
| Lumbar spine AP, 80 kVp | 0.273 | 27.3 | 359 |
| Upper G.I. | 4.1 | 410 | 2300/min |
| Coronary angioplasty | 50–150/min | 5000–15000/min | 25000/min |
| Head CT | 0.8–5 | 80–500 | 4500 |
| Abdomen CT | 6–24 | 600–2400 | 2000 |
| Dental | 0.01 | 1 | 350 |
| Electron beam CT heart | 0.14–0.3 | 14–30 | 150 |
| Mammogram | ** | ** | 700 |
| Nuclear Medicine | mSv | mrem | mrem |
| 18F-Fluorodeoxyglucose, 10 mCi | 9.99 | 999 | NA |
| 99 mTc-MAA Lung scan (perfusion only) 5 mCI | 2.03 | 203 | NA |
| 99 mTc-HDP Bone scan 20 mCi | 5.92 | 592 | NA |
| 201Tl Thallium scan 3 mCi | 25.53 | 2553 | NA |

*Seivert is the official international unit of biological radiation dose. One Sv = 100 rem.
ND = Data not available
** = Dose negligible
NA = Not applicable Depending on the age of the individual, frequency of testing, exposure time, and total dose, the diagnostic or screening imaging studies could increase the risk of somatic damage (some forms of cancer such as leukemia, breast, and thyroid) as well as genetic damage (such as with gonadal exposure) in the target population. In fact, radiation experts are beginning to call for special attention to issues of exposure from CT Scanning in younger patients (9). It should be emphasized that the risk of radiation injury produced by diagnostic doses below 0.5 rem is very small in comparison to other agents that are present in the diet or the natural environment. However, regardless of the "insignificant" risk with any individual exposure or imaging event, the total effects of ionizing radiation are on-going, cumulative over time, have the potential for lifelong expression, and may have a future generational genetic impact.

It should be anticipated that as more sophisticated imaging studies are available for diagnosis and screening, the individual small risks may add up over a lifetime. For example, nuclear medicine has been expanded to new techniques which include intravenous systemic injection of radionuclides and expose various body organs to differing radiation doses (10). The recent impact of interventional techniques often combined with surgical procedures also increases the imaging risks. Furthermore, advanced fluoroscopic imaging used for technical procedures such as percutaneous transluminal angioplasty, transhepatic cholangiography, stent and drainage placements, as well as venous access procedures may involve significant radiation exposure (11). In fact, by the year 2000 in the United States alone, about 750,000 patients underwent coronary balloon angioplasty (12). Finally, the most recent technical innovations utilized in screening procedures, such as spiral and electron beam computed tomography for heart, lung, colon, and total body scanning are new clinical areas where issues of radiation dosimetry have to be considered (13, 14).

Currently, the FAA and airlines consider flight personnel (including flight attendants) as radiation workers. As such, they are allowed a regulatory dose limit 50 times the dose limit allowable to the general public. According to recent estimates, over 400,000 frequent fliers travel over 75,000 air miles each year, which means that they will exceed radiation dose limits to the general public from galactic (cosmic) radiation during flight (15). The radiation exposure during flight varies with altitude, flight time, air route, and solar flare activity. As an example, a routine flight from New York to Chicago (highest altitude 37,000 feet) yields a radiation dose rate of 0.0039 mSv per block hour. (The block hour begins when the aircraft leaves the blocks before takeoff and ends when it reaches the blocks after landing.) A flight from Athens, Greece, to New York (highest altitude 41,000 feet) yields a radiation dose rate of 0.0063 mSv per block hour. The total radiation dose form the New York to Chicago route is 0.0089 mSv and the Athens to New York flight is 0.0615 mSv. For reference, the annual exposure limit for the general public is 1 mSv. The only remediation recommended by the FAA for radiation exposure during flight is to limit flight and avoid traveling during periods of increased solar flare activity. Airline crew members flying long-haul high-altitude routes receive, on average, greater exposures each year than do radiation workers in ground-based industries where radioactive sources or radiation-producing machines are used (16).

The United States military is aware of and concerned about potential radiation exposures to our troops. Perhaps the most obvious population at risk in the military are pilots flying long, high-altitude missions. The expected radiation doses would be in accordance with the estimates outlined above. The most recent U.S. Army study on the issue recognizes four nuclear radiation exposure risk categories of military personnel based on their likelihood and extent of exposure (17, Table 2). The Army currently has three radiation protection programs to address these risk categories. One is applied to those individuals whose duties parallel those of civilian radiation workers. These include military personnel, such as x-ray technicians, radiologists who do radiological examinations, researchers who use radionuclides, and technicians who maintain radioactive commodities, such as radiation detection instruments and calibration sources. The second applies to soldiers whose primary occupation does not usually expose them to radiation. These are soldiers who might respond to a military situation, such as that covered by Allied Command Europe Directive (ACE) 80-63, in which radiation is present, but at doses not exceeding 700 mSv. The third category applies to those situations involving extremely high radiation exposure, such as nuclear war.

TABLE 2

Revised, Low-Level Radiation Guidance for Military Operations

| Total Cumulative Dose[a] | Radiation Exposure State Category | Recommended Actions | Increased Risk of Long Term Fatal Cancer[b] |
|---|---|---|---|
| <0.5 mGy | 0 | None | None |
| 0.5–5 mGy | 1A | Record individual dose readings Initiate periodic monitoring | 1:4,000 |
| 5–50 mGy | 1B | Record individual dose readings Continue monitoring Initiate rad survey Prioritize tasks Establish dose control measure as part of operations | 1:400 |
| 50–100 mGy | 1C | Record individual dose readings Continue monitoring Update survey Continue dose-control measures Execute priority tasks only[c] | 1:200 |
| 100–250 mGy | 1D | Record individual dose readings Continue monitoring Update survey Continue dose control measures Execute critical tasks only[d] | 1:80 |
| 250–700 mGy | 1E | Record individual dose readings Continue monitoring Update survey Continue dose control measures Execute critical tasks only[d] | 1:30 |

[a]The use of the measurement millisievert is preferred in all cases. However, due to the fact that normally the military has only the capability to measure milligray (mGy), as long as the ability to obtain measurements in millisievert is not possible, U.S. forces will use milligray. For whole body gamma irradiation, 1 mGy is equal to 1 mSv. All doses should be kept as low as reasonably achievable (ALARA). This will reduce the risk to individual soldiers and will retain maximum operational flexibility for future employment of exposed soldiers.

[b]This is in addition to the 1:5 and 1:4 incidence of fatal cancer among the general population. Increased risk is given for induction of fatal cancer (losing an average of 24 years of life for personnel ages 20-30 years). It must be noted that higher radiation dose rates produce proportionately more health risks than the same total dose given over a longer period.

[c]Examples of priority tasks are those missions to avert danger to persons or to prevent damage from spreading.

[d]Examples of critical tasks are those missions required to save lives.

This study committee made four recommendations:
1) When making decisions, commanders should consider the long-term health effects that any action may have on their troops. This recommendation was extended such that it became standard operating policy.
2) The U.S. Department of Defense should develop and clearly express an underlying philosophy for radiation protection. Specifically, the committee suggested,
   a: application and adaptation of the system recommended by the International Commission of Radiological Protection,
   b: in peacetime or nonemergency situations, soldiers should be accorded the same level of protection accorded civilians, and
   c: in settings in which an intervention is required and specific numerical dose limits are neither applicable nor practical, commanders should justify the mission (there is more benefit than risk), examine competing risks, and optimize the mission (identify ways to minimize dose without jeopardizing the mission).
3) Military personnel should receive appropriate training in both radiation effects and protection. Their training will need to vary on the basis of the particular level of potential exposure and the task at hand.
4) A program of measurement, recording, maintenance, and use of dosimetry and exposure information is essential.

The programs, once again, include no protection measures other than controlling time, distance, and physical shielding.

Radiation workers experience a broad spectrum of working conditions that have radiation exposure as a normal part of the workplace environment. Examples include medical radiology workers, nuclear power plant workers, and workers who use radiation and radioactive materials in research. As mentioned above, commercial flight crews are also considered to be radiation workers. Owing to this occupational classification, radiation workers are allowed to receive 50 times the radiation dose allowed to the general public. Radiation workers also differ from the general public in that they receive training about the risks of radiation exposure and are monitored for their radiation exposure as part of their working paradigm. The nuclear regulatory commission (NRC) has established occupational dose limits as noted previously and procedures for monitoring and record-keeping. These standards and regulations rely solely on time, distance, and physical shielding as methods of radiation protection.

SUMMARY OF THE INVENTION

If it could be possible to devise a strategy to reduce the potential adverse effects of radiation exposure, it certainly seems reasonable that this approach should be undertaken regardless of how small the actual risk of injury might be. Federal law by regulatory code (C.F.R. 21 and C.F.R. 35) emphasize ALARA guidelines as they relate to occupational radiation exposure. This concept should be extended to the biological consequences of the doses received by all classes of exposed individuals, including patients. The guidelines could be referred to as DALARA (damage as low as reasonably achievable), whereby both the dose and its harmful consequences could be minimized without interfering with the efficacy, ease, or cost of diagnostic procedures, or occupational and other activities. This novel concept, supported by extensive data, is based on reducing radiation-derived free radical damage by antioxidant supplementation. Special attention needs to be given to population groups under chronic risk situations like frequent fliers, radiation workers, flight crews, and military personnel in combat theatres of operation. In these cases, episodic dosing with antioxidants is not adequate to achieve ALARA principles. These population groups should achieve and maintain higher antioxidant loads than persons with little or no expectation of radiation exposure.

In accordance with the present invention, twice daily dosing with a properly designed multiple antioxidant formulation is employed to maintain desired antioxidant loads in the body.

When chronically exposed (or chronic risk of exposure) individuals can be reasonably expected to incur an acute exposure, such as dangerous combat missions or any flight operations, they should supplement their regular antioxidant regimen with additional doses of selected antioxidants to protect against the anticipated exposure.

More particularly, the present invention is directed to a method for protecting humans in need of such protection from physical damage caused by ionizing radiation comprising administering to said humans on a defined basis prior to and after exposure to such radiation a plurality of antioxidants at a dosage level directly proportional to the radiation level likely to be encountered.

DETAILED DESCRIPTION OF THE INVENTION

Although brief medical x-rays themselves may not cause detectable damage, serial imaging, future screening studies (the importance of which cannot be currently predicted), flight exposures, military operations exposures, occupational exposures, and other factors, such as diet, disease status, and environmental exposure, and the like, may be clinically significant.

Relevant findings from basic scientific studies underscore this clinical concern. For example, a dose of 2 rem does not cause detectable mutations in normal human lymphocytes in culture. However, if the cells are irradiated with the same dose and treated with caffeine for a few hours after radiation exposure, an increased rate of cellular mutations is observed (18). This suggests that radiation-induced changes could be repaired in the normal course of events, but that subsequent exposure to caffeine impairs this normal cellular protective mechanism. In addition, a radiation dose that by itself would not be sufficient to induce cancer in an in vitro experimental system is able to do so in the presence of tumor promoters, such as phorbol ester, estrogen, and others (19-21). Furthermore, x-rays increase the incidence of cancer in cell culture by several fold when combined with chemical carcinogens, certain DNA viruses, ultraviolet radiation, or ozone exposure (22-26). Clearly, the potential hazard of even small radiation doses should not be ignored, since the target population readily interacts with agents present in the diet and environment, as well as other factors present in individual lifestyles.

Risk Categories

The following risk categories are general guidelines only and refer to acute exposures. The examples listed are not totally inclusive. The actual risk for any particular person may be modified by age and health status. The actual designation for all persons should be determined by healthcare or radiation physics professionals.

Population groups experiencing chronic radiation exposure risk, such as radiation workers (including commercial and military flight crews and field combat personnel), should maintain a higher baseline antioxidant load by taking a multiple antioxidant formulation (SEVAK) two times a day. They should then take the appropriate radioprotective formulation when the acute risk of exposure is expected (daily if necessary). Categories 2-4 are equivalent with respect to formulation and can be regarded to be adequate for exposures less than 15 mSv effective dose when taken on a daily basis along with SEVAK. The categories vary with respect to dose schedule when used for acute exposures only.

Category 1: Effective Dose 0.5 mSv or Less

For example: chest x-ray, dental x-ray, abdominal x-ray, skeletal plain films, most commercial flight passengers.

Category 2: Effective Dose 0.5-5 mSv

For example: diagnostic/screening computed tomography, urologic imaging, mammography, flight crews (commercial and military) and other radiation workers.

Category 3: Internal Radionuclide Exposures

For example: radionuclide imaging.

Category 4: Effective Dose 5-15 mSv

For example: limited diagnostic fluoroscopy (upper GI series, cholangiography, barium enema).

Category 5: Effective Dose Greater Than 15 mSv-250 mSv

For example: prolonged fluoroscopy/interventional radiology (coronary angiography, cerebral angiography, transluminal angioplasty) and some military personnel in combat operations (ground troops and seamen).

Category 6: Effective Dose 1000-2000 mSv

For example: radiation workers, civilian populations at risk near nuclear reactor sites, and at risk military personnel in overseas theatres of operation.

Category 7: Effective Dose Greater Than 2000 mSv (not Exceeding Bone Marrow Syndrome Doses)

For example: radiation workers, civilian populations at risk near nuclear reactor sites, and at risk military personnel in overseas theatres of operation.

Hereinafter, the term "imaging study" will be employed to include chest x-ray, dental x-ray, abdominal x-ray, skeletal plain films, diagnostic/screening computed tomography, urologic imaging, mammography, radionuclide imaging, limited diagnostic fluoroscopy, prolonged fluoroscopy/interventional radiology, and the like.

| Baseline Formulation (SEVAK) | |
|---|---|
| (Daily dose is contained in 4 capsules. Normally used for personnel in categories 6 and 7 and for personnel in category 2 who are member of flight crews and radiation workers.) | |
| Vitamin A (palmitate) | 5,000 I.U. |
| Beta-carotene (from natural *D. salina*) | 15 mg |
| Vitamin D-3 (cholecalciferol) | 400 I.U. |
| Natural source Vitamin E | |
| (d-alpha tocopherol) | 100 I.U. |
| (d-alpha tocopheryl acid succinate) | 100 I.U. |
| Buffered Vitamin C (calcium ascorbate) | 500 mg |
| Thiamine mononitrate | 4 mg |
| Riboflavin | 5 mg |
| Niacinamide ascorbate | 30 mg |
| d-calcium pantothenate | 10 mg |
| Pyridoxine hydrochloride | 5 mg |
| Cyanocobalamin | 10 µg |
| Folic Acid (Folacin) | 800 µg |
| D-Biotin | 200 µg |
| Selenium (l-seleno-methionine) | 100 µg |
| Chromium picolinate | 50 µg |
| Zinc glycinate | 15 mg |
| Calcium citrate | 250 mg |
| Magnesium citrate | 125 mg |

| Radioprotective Formulations: (boost formulations) | |
|---|---|
| For Category 1 Personnel: | |
| vitamin C (calcium ascorbate) | 250 mg |
| natural source vitamin E | 200 I.U. |
| (d-alpha tocopheryl acid succinate) | |
| N-acetyl cysteine | 250 mg |
| Complete dosage to be taken 1 hour prior to an imaging study. | |
| For Category 2 Personnel: | |
| vitamin C (calcium ascorbate) | 500 mg |
| natural source vitamin E | 400 I.U. |
| (d-alpha tocopheryl acid succinate) | |
| N-acetyl cysteine | 250 mg |
| beta-carotene (from natural *d. salina*) | 15 mg |
| alpha lipoic acid | 30 mg |
| Complete dosage to be taken 1 hour prior to an imaging study or prior to each flight. | |
| For Category 3 Personnel: | |
| vitamin C (calcium ascorbate) | 500 mg |
| natural source vitamin E | 400 I.U. |
| (d-alpha tocopheryl acid succinate) | |
| N-acetyl cysteine | 250 mg |
| beta-carotene (from natural *d. salina*) | 15 mg |
| alpha lipoic acid | 30 mg |
| Complete dosage to be taken 1 hour prior to an imaging study and 24 hours and 48 hours after the imaging study. | |
| For Category 4 Personnel: | |
| vitamin C (calcium ascorbate) | 500 mg |
| natural source vitamin E | 400 I.U. |
| (d-alpha tocopheryl acid succinate) | |
| N-acetyl cysteine | 250 mg |
| beta-carotene (from natural *d. salina*) | 15 mg |
| alpha lipoic acid | 30 mg |
| Complete dosage to be taken 24 hours and 1 hour prior to an imaging study and 24 hours after the imaging study. | |
| For Category 5 Personnel: | |
| vitamin C (calcium ascorbate) | 500 mg |
| natural source vitamin E | 400 I.U. |
| (d-alpha tocopheryl acid succinate) | |
| N-acetyl cysteine | 500 mg |
| beta-carotene (from natural *d. salina*) | 30 mg |
| alpha lipoic acid | 60 mg |
| Complete dosage to be taken 48 hours, 24 hours, and 1 hour prior to an imaging study and 24 hours after the imaging study. | |
| For Category 6 Personnel: | |
| vitamin C (calcium ascorbate) | 1000 mg |
| d-alpha tocopheryl acid succinate | 400 I.U. |
| alpha tocopherol | 200 I.U. |
| N-acetyl cysteine | 500 mg |
| beta-carotene (from natural *d. salina*) | 50 mg |
| alpha lipoic acid | 100 mg |

-continued

Complete dosage to be taken prior to anticipated exposure or as soon as possible after actual exposure. Continue complete dosage daily for seven days after exposure.
For Category 7 Personnel:

| | |
|---|---|
| vitamin C (calcium ascorbate) | 2000 mg |
| d-alpha tocopheryl acid succinate | 600 I.U. |
| alpha tocopherol | 200 I.U. |
| N-acetyl cysteine | 1000 mg |
| beta-carotene (from natural d. salina) | 100 mg |
| alpha lipoic acid | 150 mg |

Complete dosage to be taken prior to anticipated exposure or as soon as possible after actual exposure. Continue complete dosage daily for fourteen days after exposure.

It has been estimated that approximately 70-80% of the cellular damage induced by ionizing radiation is caused by free radicals (23). Therefore, it would be prudent to use agents that would quench these substances formed during x-ray exposure and protect the cells, organs, and total body from such injury.

Since World War II, extensive studies have been undertaken to identify radioprotective compounds that have been shown to be effective when administered before exposure to irradiation (2, 27). It is important to note that such compounds do not protect cells or organisms if they are administered after the ionizing radiation exposure. For modest radiation dose levels, the protective agents can be absorbed rapidly enough that they could be effective when given immediately before the exposure (within an hour or two). For higher levels of radiation dosage, it might be more desirable to achieve an established steady state of antioxidant concentration in the tissues initially, and then provide a booster dose of radioprotective agent immediately prior to exposure.

Research has determined that sulfhydryl (SH) compounds such as cysteamine, cystamine, and glutathione are among the most important and active intracellular antioxidants. Cysteamine protects animals against bone marrow (2, 31) and gastrointestinal (32) radiation syndromes. The rationale for the importance of SH compounds is further supported by observations in mitotic cells. These are the most sensitive to radiation injury in terms of cell reproductive death and are noted to have the lowest level of SH compounds. Conversely, S-phase cells, which are the most resistant to radiation injury using the same criteria, have demonstrated the highest levels of inherent SH compounds. In addition, when mitotic cells were treated with cysteamine, they became very resistant to radiation (33). It has also been noted that cysteamine may directly protect cells against induced mutations (2). Unfortunately, cysteamine is extremely toxic when administered to human beings and, therefore, cannot itself be utilized in a radioprotective antioxidant regimen.

Thus, other SH compounds sharing the same antioxidant characteristics must be considered. Glutathione is a very effective antioxidant. However, when ingested by human beings it is completely hydrolyzed in the intestine and, therefore, can not be used as a radioprotective agent. However, N-acetylcysteine (NAC) and alpha lipoic acid actively increase the intracellular levels of glutathione without causing any toxicity. These rapidly absorbed compounds are tolerated by humans very well and would provide protection against ionizing radiation damage when given prior to the exposure. Indeed, these agents have also been shown to be of radioprotective value in experimental systems (31-35). Additional antioxidants such as vitamin E (d-alpha tocopheryl succinate), vitamin C (as calcium ascorbate) and the carotenoids (particularly natural beta-carotene) have been shown to be of marked radioprotectant value in animals and in humans (2, 36-50). A very recent report by the Armed Forces Radiobiology Research Institute showed good protection by vitamin E against lethal doses of cobalt-60 in mice (51).

The natural beta-carotene was selected because it most effectively reduces radiation-induced transformation in mammalian cells in culture (47). The d-alpha tocopheryl succinate form of vitamin E was selected because it is the most effective form of this micronutrient (52) and also actively reduces the incidence of radiation-induced transformation in mammalian cells (53, 54). This form of vitamin E is a more effective antioxidant than the more commonly utilized alpha tocopherol or other mixtures of tocopherols (55). Vitamin C as calcium ascorbate is beneficial because it is the most effective nonacidic form available for human use and, therefore, is less likely to cause stomach upset, diarrhea, and other problems that are observed in some individuals when taking therapeutic doses of vitamin C.

The most effective antioxidant approach to the free radical damage related to ionizing radiation-induced injury must utilize multiple micronutrients. It has been determined that multiple antioxidants are more effective than the individual agents themselves, and we propose this approach for several reasons. It is known that vitamin C and vitamin E are synergistic as antioxidants against free radicals because they are able to protect both the aqueous and lipid environments of the cells respectively. Indeed, one study has shown that oral intake of both vitamin C and vitamin E reduces the levels of fecal mutagens formed during digestion more than that produced by either of the individual antioxidants (56). It also must be recognized that oxygen level may vary widely within the tissues of whole organs or within the individual cells. This is especially true during the biologic insults that may occur with radiation-induced damage. It is known that beta-carotene acts more effectively as an antioxidant in high oxygen pressures, whereas vitamin E is a more effective antioxidant at reduced oxygen pressures (57).

Finally, the body produces several types of free radicals (a myriad of oxygen-derived and nitrogen-derived species) during exposure to ionizing radiation. Clearly, each antioxidant has a different affinity for each specific class of free radicals. In a parallel manner, a combination of antioxidants is more effective in reducing the growth of tumor cells than the individual agents themselves (58). Therefore, to provide the most effective overall micronutrient approach to protect against radiation injury, a multiple component protocol utilized with a risk-based strategy seems essential and rational.

In the interest of clarity and conserving space, references in the foregoing have been given by number, parenthetically. These numbers relate to the following:

1. Prasad KN: *Human Radiation Biology.* Harper and Row, New York, N.Y., 1974.
2. Prasad KN: *Handbook of Radiobiology,* CRC Press, Boca Raton, Fla., 1994.
3. Brenner D J, Elliston C D, Hall E J, Berdon W E: Estimated risks of radiation-induced fatal cancer from pediatric CT, Am J Roentgenol 176: 289-296, 2001.
4. United Nations Scientific Committee on the Effects of Atomic Radiation: Sources and Effects of Ionizing Radiation: UNSCEAR Report to the General Assembly, with Scientific Annexes, 1993.
5. International Council for Radiation Protection, ICRP publication 33, 1982.

6. *FDA Centers for Radiologic Health Handbook:* Selected Tissue Doses for Fluoroscopic and Cineangiographic Examination of the Coronary Arteries, 1995.
7. FDA and Mayo Clinic values of X-ray doses, mww.mayohealth.org, Mayo Foundation for Medical Education and Research, 2000.
8. Radiation Dose Estimates for Radiopharmaceuticals, Radiation Internal Dose Information Center, Oak Ridge Institute for Science and Education, 1996.
9. Paterson A, Frush D P, Donnelly L F: Helical CT of the body: are settings adjusted for pediatric patients? Am J Roentgenol 176: 297-301, 2001.
10. *Drug Information for the Healthcare Professional,* Rockville, Md.: United States Pharmacopeial Convention, Inc: 2457, 1991.
11. Cascade P N, Peterson L E, Wajszczuk W J, Mantel J: Radiation exposure to patients undergoing percutaneous transluminal coronary angioplasty. Am J Cardiol 59: 996-997, 1987.
12. Angioplasty and Cardiac Revascularization Treatment and Statistics, American Heart Association, Heart and Stroke Statistical Update, 2001.
13. Rumberger J A, Sheedy P F III, Breen J F, Schwartz R S: Coronary calcium as determined by electron beam computed tomography and coronary disease on angiogram: effect of patient's sex on diagnosis. Circulation 91: 1363-1367, 1995.
14. Stanford W, Thompson B H, Weiss R M: Coronary artery calcification: clinical significance and current methods of detection. Am J Roentgenol. 161: 1139-1146, 1993.
15. Barish R J: In-flight radiation: Counseling patients about risk. J Am Board Fam Pract 12:195, 1999.
16. Barish R J: Health physics concerns in commercial aviation. Health Phys 59: 199, 1990.
17. Institute of Medicine Report: Potential radiation exposure in military operations: Protecting the soldier before, during, and after. http://www.nap.edu/openbook/0309064392/mtml/55.html National Academy Press, 2000.
18. Puck T T, et al: Caffeine enhanced measurement of mutagenesis by low levels of gamma-irradiation in human lymphocytes. Somatic Cell & Molec Genet 19: 423, 1993.
19. Little J B: Influence of non-carcinogenic secondary factors on radiation carcinogenesis. Radiat Res 87: 240, 1981.
20. Holtzman S, Stone J P, Schellabarger C J: Synergism of estrogen and x-rays in mammary carcinogens in female ACI rats. J Natl Cancer Inst 67: 455, 1981.
21. Knekt P, Reunanen A, Takkunen H: Body iron stores and risk of cancer. Int J Cancer 56: 379, 1994.
22. DiPaolo J A, Donovan P J, Popewseu N C: Kinetics of syrian hamster cells during x-irradiation enhancement of transformation in vitro by chemical carcinogens. Radiat Res 66: 310, 1976.
23. Stoker M: Effect of x-irradiation on susceptibility of cells to transformation by polyoma virus. Nature (Lond) 200: 756, 1963.
24. Pollack E J, Todaro G J: Radiation enhancement of SV-40 transformed 3T3 and human cells. Nature (Lond) 219: 520, 1968
25. DiPaolo J A, Donovan P J: In vitro morphological transformation of syrian hamster cells by U.V.-irradiation is enhanced by x-irradiation and unaffected by chemical carcinogens. Int J Radiat Biol 30: 41, 1976.
26. Borek C, Zaider N, Ong A: Ozone acts alone and synergistically with ionizing radiation to induce in vitro neoplastic transformation. Carcinogenesis 7: 1611, 1986.
27. Hall E J: *Radiobiology for the Radiologist.* J. B. Lippincott Co. Philadelpha, Pa., 1994.
28. Thomson J F: *Radiation Protection in Mammals.* Reinhold, New York, N.Y., 1962.
29. Prasad K N, Kollmorgen G M, Kent T H, Osborne J W: Protective effect of beta-mercaptoethylamine and mesenteric vessel clamping on intestinal irradiated rats. Int J Radiat Biol. 6: 257, 1963.
30. Sinclair W K: Cysteamine: Different x-ray protective effect on Chinese hamster cells during the cell cycle. Science 159: 442, 1968.
31. Wolf S: Radiation Genetics. In: *Mechanisms in Radiobiology,* Errera M and Forsberg A., Eds. Academic Press, New York, p. 441, 1961.
32. Sminia P, Van der Kracht A H, Frederiks W M, Jansen W: Hyperthermia, radiation, carcinogenesis and the protective potential of vitamin A and N-acetylcysteine. J Cancer Res & Clin Oncol 122: 343, 1996.
33. Killoran P L, Walleczek J: Inhibition of store-operated calcium entry in human lymphocytes in radiation protection: protection by glutathione. Radiat Res 152: 611, 1999.
34. Ushakova T, Melkonyan H, Nikonova L, Afanasyev V, Gaziev A I, Mudrik N, Bradbury R, Gogvadze V: Modification of gene expression by dietary antioxidants in radiation-induced apoptosis of mice splenocytes. Free Radical Biol. & Med 26: 887, 1999.
35. Ramakrishna N, Wolfe W W, Catravas G N: Radioprotection of hematopoietic tissues in mice by lipoic acid. Radiat Res 130: 360, 1992.
36. Weiss J F, Landauer M R: Radioprotection by antioxidants. Ann New York Acad. Sci 899: 44, 2000.
37. Motlu-Turkoglu U, Erbil Y, Oztezcan S, Olgac U, Tokev G, Uysal M: The effect of selenium and/or vitamin E treatment on radiation-induced intestinal injury in rats. Life Sciences 66: 1905, 2000.
38. Konopacka M, Widel M, Rzeszowska-Wolny J: Modifying effect of vitamin C, E and beta-carotene against γ-ray-induced DNA damage in mouse cells. Mutation Res 417: 85, 1998.
39. Paranich A V, DeConcecao A., Buga E V, Kopylov A V: The role of fat soluble vitamin A and vitamin E in preventing the biological effects of ionizing radiation in rat tissue. Radiobiologia 32: 743, 1992.
40. O'Connor M K, Malone J F, Moriarity M and Mulgrew S A: Radioprotective effect of vitamin C observed in Chinese hamster ovary cells. Brit J Radiol 50: 587, 1977.
41. Harapanhalli R S, Yaghmai V., Guiliani D., Howell R W, Rao D V: Antioxidant effect of vitamin C in mice following x-irradiation. Res Commun Mol Pathol. & Pharmacol. 94: 271, 1996.
42. Narra V R, Harapanhalli R S, Howell R W, Sastry K S, Rao D V: Vitamins as radioprotector in-vivo. Protection by vitamin C against internal radionuclides in mouse testes: implications to the mechanism of damage caused by the Auger effect. Radiat Res 137: 394, 1994.
43. El-Habit O H, Saada H N, Azab K S, Abdel-Rahman M., El-Malah D F: The modifying effect of beta-carotene on γ-radiation-induced elevation of oxidative reactions and genotoxicity in male rats. Mutation Res 466: 179, 2000.
44. Ben-Amotz A., Yatzib S., Sela M., Greenbers S., Rachmilevich B., Scwarzman M., Weshler Z: Effect of natural beta-carotene supplementation in children exposed to radiation from the Chernobyl accident. Radiat & Envirn Biophys 37: 187, 1998.

45. Ni O G, Pei Y: Effect of beta-carotene on $^{60}$Co-gamma-induced mutation at T-lymphocyte hypoxanthine-guanine phosphoribosyl transferase locus in rats. Acta Pharmacologic Sinica 18: 535, 1997.
46. Umegaki K., Uramoto H., Suzuki J., Esashi T: Feeding mice palm carotene prevents DNA damage in bone marrow and reduction of peripheral leukocyte counts and enhances survival following x-ray radiation. Carcinogenesis 18: 1943, 1997.
47. Kennedy A R, Krinsky N I: Effect of retinoids, beta-carotene and canthaxanthine on U.V. and x-ray-induced transformation of C3H10T1/2 cells in vitro. Nutr Cancer 22: 219, 1994.
48. Riabchenko N I, Ivnnik B P, Korokhorina V A, Riabchenko V I, Sinkova R V, Grosheva I P, Dzikouskaia L A: The molecular, cellular and systemic mechanisms of the radioprotective action of multivitamin antioxidant complexes. Radiatsionnaia Biologiia, Radioecologiia 36: 895, 1996 (Russian).
49. Gaziev A I, Sologub G R, Fomenka L A, Zaichkins S I, Kosyakova N I, Bradbury R J: Effect of vitamin-antioxidant micronutrients on the frequency of spontaneous and in vitro gamma-ray-induced micronuclei in lymphocytes of donors: the age factor. Carcinogenesis 17: 493, 1996.
50. Gazier A I, Podlutsky A J, Panfilov B M, Bradbury F J: Dietary supplements of antioxidants reduce hprt mutant frequency in splenocytes of aging mice. Mutation Res 338: 77, 1995.
51. Kumar, K. S., Srinivasan, V., Toles, R., Jobe, L., and Seed, T. M. Nutritional approaches to radioprotection: vitamin E. Military Medicine., 167: 57-59, 2002.
52. Prasad K N, Edwards-Prasad J: Effect of tocopherol (vitamin E) acid succinate on morphological alterations and growth inhibition in melanoma cells in culture. Cancer Res 42: 550, 1982.
53. Rander B S, Kennedy A N: Suppression of x-ray-induced transformation by vitamin E in mouse C3H10T1/2 cells. Cancer Lett 32: 2, 1986.
54. Borek C., Ong A., Mason H., Donahue L., Bigalow J E: Selenium and vitamin E inhibit radiogenic and chemically-induced transformation in vitro via different mechanisms. Proc Nat Acad Sci USA. 83: 1490, 1986.
55. Carini R., Poli G., Dianzani M U, Maddix S P, Slater T F, Cheeseman K H: Comparative evaluation of the amount of the antioxidant activity of alpha-tocopherol, alpha-tocopherol polyethylene glycol 1000 succinate and alpha-tocopherol succinate in isolated hepatocytes and liver microsomal suspensions. Biochem Pharmacol 39: 1597, 1990.
56. Dion P W, Bright-See E, Smith C C, et al: The effect of dietary ascorbic acid and alpha-tocopherol on fecal mutagenicity. Mutation Res 102: 27, 1982.
57. Krinsky N: Antioxidant functions of carotenoids. Free Radical Biol. Med 7: 617, 1989.
58. Prasad K N, Hernandez C, Edwards-Prasad J, et al: Modification of the effect of tamoxifen, cisplatin, DTIC and interferon alpha-2b on human melanoma cells in culture by a mixture of vitamins. Nutr Cancer 22: 233, 1994.

What is claimed is:

1. A formulation consisting essentially of:

| | |
|---|---|
| Vitamin A (palmitate) | 5,000 I.U. |
| Beta-carotene (from natural D. salina) | 15 mg |
| Vitamin D-3 (cholecalciferol) | 400 I.U. |
| Natural soucre Vitamin E | |
| (d-alpha tocopherol) | 100 I.U. |
| (d-alpha tocopheryl acid succinate) | 100 I.U. |
| Buffered Vitamin C (calcium ascorbate) | 500 mg |
| Thiamine mononitrate | 4 mg |
| Riboflavin | 5 mg |
| Niacinamide ascorbate | 30 mg |
| d-calcium pantothenate | 10 mg |
| Pyridoxine hydrochloride | 5 mg |
| Cyanocobalamin | 10 µg |
| Folic Acid (Folacin) | 800 µg |
| D-Biotin | 200 µg |
| Selenium (1-seleno-methionine) | 100 µg |
| Chromium picolinate | 50 µg |
| Zinc glycinate | 15 mg |
| Calcium citrate | 250 mg |
| Magnesium citrate | 125 mg | and a booster formulation selected from a group consisting essentially of 1000 mg of vitamin C, 400 international units of d-alpha tocopheryl acid succinate, 200 international units of alpha tocopherol, 500 mg of N-acetyl cysteine, 50 mg of beta-carotene, and 100 mg of alpha lipoic acid, wherein said formulation is designed to reduce the risk in humans exposed to ionizing radiation of becoming subjected to at least one condition selected from the group consisting essentially of radiation-induced acute leukemia, breast cancer, and thyroid cancer.

2. The formulation of claim 1 wherein said dosage is taken prior to anticipated exposure.

3. The formulation of claim 1 wherein said dosage is taken after exposure.

4. The formulation of claim 1 wherein said formulation is taken by user after exposure for a period of at least seven days.

5. The formulation of claim 1 wherein said formulation is designed for a human who receives an effective dose of ionizing radiation of 0.5 mSv or less.

6. The formulation of claim 1 wherein said formulation is designed for a human who receives an effective dose of ionizing radiation of 0.5-5 mSv.

7. The formulation of claim 1 wherein said formulation is designed for a human who receives internal radionuclide exposures.

* * * * *